United States Patent
Warren

(10) Patent No.: US 11,951,260 B2
(45) Date of Patent: *Apr. 9, 2024

(54) EFFICIENT ENRICHED OXYGEN AIRFLOW SYSTEMS AND METHODS

(71) Applicant: WEARAIR VENTURES, INC., Melville (CA)

(72) Inventor: John Warren, Melville (CA)

(73) Assignee: WEARAIR VENTURES, INC., Melville (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/850,804

(22) Filed: Jun. 27, 2022

(65) Prior Publication Data

US 2022/0339389 A1 Oct. 27, 2022

Related U.S. Application Data

(63) Continuation of application No. 17/141,085, filed on Jan. 4, 2021, now abandoned.
(Continued)

(51) Int. Cl.
| | | |
|---|---|---|
| *A61M 16/10* | (2006.01) | |
| *A61M 16/00* | (2006.01) | |
| *A61M 16/06* | (2006.01) | |

(52) U.S. Cl.
CPC ........ *A61M 16/101* (2014.02); *A61M 16/024* (2017.08); *A61M 16/0672* (2014.02);
(Continued)

(58) Field of Classification Search
CPC ............ A61M 16/101; A61M 16/0672; A61M 16/024; A61M 2016/0036;
(Continued)

(56) References Cited

U.S. PATENT DOCUMENTS

| | | |
|---|---|---|
| 3,533,221 A | 10/1970 | Takaaki |
| 4,971,609 A | 11/1990 | Pawlos |
| (Continued) | | |

FOREIGN PATENT DOCUMENTS

| | | |
|---|---|---|
| CA | 2810669 | 3/2012 |
| CN | 202322372 | 7/2012 |
| (Continued) | | |

OTHER PUBLICATIONS

Non-Final Office Action dated Apr. 30, 2021 for U.S. Appl. No. 17/141,085.
(Continued)

*Primary Examiner* — Valerie L Woodward
*Assistant Examiner* — Paige Kathleen Bugg
(74) *Attorney, Agent, or Firm* — Len S. Smith; Julie E. Kurzrok; Transformative Legal LLC

(57) ABSTRACT

The invention provides new systems/methods for providing oxygen to chronically ill patients, such as COPD patients, through a more efficient portable oxygen concentrator ("POC") that at least sometimes delivers an enriched airflow having a significantly lower overall oxygen concentration than that administered by typical POCs. In aspects, the methods/systems of the present invention are configured to automatically switch from pulse delivery to continuous delivery, from continuous delivery to pulse delivery, or any combination thereof, at least once per day, when certain conditions occur. Methods/system can comprise the ability to switch between mode(s) comprising delivery of a moderately enriched oxygen airflow (MEOA) and mode(s) comprising delivery of intensively enriched oxygen airflow, highly enriched oxygen airflow, or both, and back again, based on one or more parameters.

15 Claims, 2 Drawing Sheets

Related U.S. Application Data

(60) Provisional application No. 62/995,224, filed on Jan. 21, 2020.

(52) U.S. Cl.
CPC ............... *A61M 2016/0036* (2013.01); *A61M 2016/1025* (2013.01); *A61M 2202/0057* (2013.01); *A61M 2202/0208* (2013.01); *A61M 2202/0266* (2013.01); *A61M 2205/3334* (2013.01)

(58) Field of Classification Search
CPC .. A61M 2016/1025; A61M 2202/0057; A61M 2202/0208; A61M 2202/0266; A61M 2205/3334
USPC ..................................................... 128/205.12
See application file for complete search history.

(56) References Cited

U.S. PATENT DOCUMENTS

| | | | |
|---|---|---|---|
| 6,520,176 | B1 | 2/2003 | Dubois |
| 6,651,658 | B1 | 11/2003 | Hill |
| 6,691,702 | B2 | 2/2004 | Appel |
| 7,763,103 | B2 | 7/2010 | Dolensky |
| 8,894,751 | B2 | 11/2014 | Galbraith |
| 9,717,876 | B2 | 8/2017 | Wilkinson |
| 9,974,918 | B2 | 5/2018 | Armstrong |
| 9,974,919 | B2 | 5/2018 | Richard |
| 10,583,265 | B2 | 3/2020 | Whitcher |
| 10,799,663 | B1 | 10/2020 | Oddo |
| 2006/0174878 | A1* | 8/2006 | Jagger .................... A61M 16/10 128/201.25 |
| 2006/0185668 | A1* | 8/2006 | Jagger ................. A61M 16/101 128/203.26 |
| 2006/0230931 | A1 | 10/2006 | Bliss |
| 2010/0116270 | A1* | 5/2010 | Edwards ............... A61M 16/12 128/204.26 |
| 2011/0197890 | A1 | 8/2011 | Jagger |
| 2011/0247620 | A1* | 10/2011 | Armstrong ........ A61M 16/0677 128/207.18 |
| 2012/0000462 | A1 | 1/2012 | Edwards |
| 2012/0266883 | A1 | 10/2012 | Taylor |
| 2014/0345609 | A1* | 11/2014 | Whitcher ............ C01B 13/0259 128/202.26 |
| 2015/0059764 | A1 | 3/2015 | Metelits |
| 2015/0083121 | A1 | 3/2015 | Fisher |
| 2020/0179638 | A1* | 6/2020 | Oddo .................. B01D 53/047 |
| 2020/0306486 | A1 | 10/2020 | Oddo |
| 2020/0360644 | A1* | 11/2020 | Westfall ............... B01D 53/053 |
| 2021/0093824 | A1* | 4/2021 | Colefax .............. A61M 16/208 |
| 2021/0196916 | A1 | 7/2021 | Rauker |
| 2023/0023722 | A1* | 1/2023 | Warren ............... A61M 16/024 |

FOREIGN PATENT DOCUMENTS

| | | |
|---|---|---|
| EP | 1401557 | 3/2004 |
| EP | 1637209 | 3/2006 |
| EP | 3193996 | 7/2017 |
| GB | 955894 | 4/1964 |
| JP | 2007536759 | 5/2008 |
| JP | 2008517638 | 5/2008 |
| JP | 2010227517 | 10/2010 |
| WO | WO2011127314 | 10/2011 |
| WO | WO2015015852 | 2/2015 |
| WO | WO2019202390 | 10/2019 |
| WO | WO2020037375 | 2/2020 |

OTHER PUBLICATIONS

Final Office Action dated Aug. 17, 2021 for U.S. Appl. No. 17/141,085.

Non-Final Office Action dated Dec. 27, 2021 for U.S. Appl. No. 17/141,085.

Sakaue, et al., "Oxygen Inhalation Using an Oxygen Concentrator in Low-Pressure Environment Outside of a Hospital", The American Journal of Emergency Medicine, vol. 26, Issue 9, p. 981-984, Nov. 1, 2008.

Oxygen Concentrator/SET, S0002047 Product Information.

Miller, GW and Fenner, JE. "A "Smart" Molecular Sieve Oxygen Concentrator with Continuous Cycle Time Adjustment", Air Force Materiel Command Brooks Air Force Base, Texas, Apr. 1996; Final Technical Paper for Period October Oct. 1989-Oct. 1992.

Katz, et al., "An in silico analysis of oxygen uptake of a mild COPD patient during rest and exercise using a portable oxygen concentrator", International Journal COPD, 2016:2427-2434.

Hardavella, et al., "Oxygen Devices and Delivery System", Breathe, Sep. 2019, vol. 15, No. 3.

Williams, Paul Robert, "Characterization and Feasibility of a Portable Oxygen Concentrator for use with a Mass Casualty Ventilator", thesis for Boise State University, Dec. 2013.

Driscoll, et al., "Emergency Oxygen Therapy for the COPD Patient", Emerg Med J 2001; 18:333-339.

Brill, et al, "Oxygen Therapy in Acute Exacerbations of Chronic Obstructive Pulmonary Disease" International Journal of COPD, 2014:9, 1241-1252.

\* cited by examiner

EFFICIENT ENRICHED OXYGEN AIRFLOW SYSTEMS AND METHODS

CROSS-REFERENCE TO RELATED APPLICATIONS

This application is a continuation of U.S. Non-Provisional patent application Ser. No. 17/141,085 entitled "Efficient Enriched Oxygen Airflow Systems and Methods", filed Jan. 4, 2021 (abandoned), which claims priority to U.S. Provisional Patent Application No. 62/995,224, entitled "Method to Increase Blood Oxygen Concentration While Reducing Oxygen Concentrator Work," filed Jan. 21, 2020. This application claims the benefit of priority to, and incorporates by reference the entirety of, these above-referenced priority applications.

FIELD OF THE INVENTION

The invention relates to methods for treating diseases, such as chronic obstructive pulmonary disease and related or similar conditions, through new and surprisingly effective methods for the delivery of oxygen enriched airflows under conditions that are more efficient than current leading methods of oxygen delivery.

BACKGROUND OF THE INVENTION

Hypoxemia is a condition characterized by low levels of oxygen in the blood, such as in the arteries. Hypoxemia occurs when the body's demand for oxygen exceeds the supply and the lungs are unable to replenish the oxygen, causing the oxygen level in the blood to fall below normal. Hypoxemia can arise from many factors including high altitude, heart disease, and respiratory problems, such as, e.g., chronic obstructive pulmonary disease ("COPD"), asthma, sleep apnea, cystic fibrosis, acute respiratory distress syndrome ("ARDS"), and lung disease.

Individuals whose blood oxygen levels are lower than normal often require the assistance of an external oxygen device to replace the oxygen. Generally, these devices are one of three types: oxygen cylinders, stationary oxygen concentration devices, or portable oxygen concentration devices ("portable oxygen concentrators" or "POCs"). Oxygen cylinders store a limited amount of pressurized oxygen, are quite heavy, and require frequent refilling and/or replacing. Oxygen concentrators, on the other hand, continuously bring in ambient air, compress and treat it, and then release the oxygen to the user. Portable oxygen concentrators purify and compress ambient air while removing nitrogen, converting the ambient air from the normal 21% oxygen to 90-95% pure oxygen. Unlike the cylinders, oxygen concentrators do not use a tank, and do not require refilling or replacing. Stationary oxygen concentrators (like oxygen cylinders) are useful when continuous oxygen flow is needed, such as when the user is sleeping or sitting still. When oxygen is administered via continuous flow, and the flow rate remains the same regardless of the number of breaths or the deepness/force the breaths of the user.

As suggested by their name, portable oxygen concentrators are typically smaller, and more lightweight as compared to the stationary oxygen concentrators and have the added benefit of providing the user with freedom and mobility. However, the amount of oxygen that can be produced by a portable concentrator over extended periods of time is limited due to energy requirements, size and weight of the compressor component, and battery life. Portable oxygen concentrators can be a continuous flow type or a pulse dose type (e.g., where oxygen is delivered to the user only when the user inhales).

Oxygen concentrators are frequently associated with COPD patients. COPD is a group of chronic lung conditions, including emphysema and chronic bronchitis, that cause airways to become obstructed or blocked resulting in breathing-related issues. In chronic bronchitis, the bronchi (airways) become inflamed and irritated, causing them to fill with mucous and making it difficult for the lungs to bring in oxygen and rid carbon dioxide. In emphysema, the alveoli (air sacs) become irreparably damaged causing them to rupture, making a large air pocket instead of many smaller ones and causing air to become trapped in the damaged sacs while the lungs become overfilled. Both conditions cause air to be trapped in the lungs, thus preventing the lungs from fully emptying and causing the common symptoms of coughing, wheezing, excess phlegm and mucus, shortness of breath, and difficulty taking a deep breath.

COPD patients often have difficulty walking or climbing stairs and may have co-existing chronic conditions, such as arthritis, congestive heart failure, diabetes, coronary heart disease, stroke, and asthma. As a result, the challenges related to sufficient, portable oxygen supply for these patients are especially difficult, as the amount of oxygen a COPD patient needs is high, and with existing oxygen concentration systems, producing that much oxygen in a mobile device takes a lot of energy which means a big compressor and a heavier overall unit. Such large and heavy units are especially problematic for these patients, and this can create a downward spiral; COPD patients lack the mobile oxygen sources which can provide opportunities for movement; lack of movement can exacerbate poor breathing conditions e.g., due to lack of exercise.

Typically, patients receiving supplemental oxygen use a portable machine, which administers a pulsed flow of oxygen when the user is mobile, and a separate, larger stationary machine or oxygen tank administering continuous oxygen while the patient sleeps or is stationary at home. Continuous oxygen administration requires a substantial amount of work by the compressor and the machine in general, hence why these machines are bulkier and heavier. Commercially available portable oxygen concentrators deliver highly oxygen-enriched airflows, comprising 90%±3% oxygen concentration. Most patent and technical disclosures in the art also disclose the use of enriched oxygen airflows comprising at least 80% oxygen (see, e.g., U.S. Pat. Appl. Pub. No. 2011/0197890 (at least 85% oxygen concentration), U.S. Pat. Appl. Pub. No. 2012/0000462 (describing enriched oxygen airflows containing 82-93% oxygen), U.S. Pat. Appl. Pub. No. 2006/0185668 (describing enriched oxygen airflows of 85-95%), and Chinese Pat. Appl. Pub. No. CN202322372U (describing the desire to achieve oxygen concentrations of greater than 90%)). Enriching airflows to such high oxygen concentrations requires significant energy expenditure, limiting battery life and, accordingly, mobility, due to size/weight, and increased expense associated with operating such devices. Several other patent documents and a few publications, however, at least make mention of enriched oxygen airflows with less than 80% or 90% oxygen concentration. For example, U.S. Pat. No. 9,974,919 to Richard et al. (and related U.S. Pat. No. 9,974,918 to Armstrong et al.) is directed to portable oxygen concentrators that deliver oxygen via either continuous or pulse delivery. While nearly all of the focus of the patent is directed to reducing the energy consumption of the concentrators by using minimum oxygen purity levels of typically 85%-90% oxygen concentration, consistent with commercially known portable oxygen concentrators (which typically deliver about 90% oxygen), Richard does include a single statement that the purity level of the enriched oxygen airflow described therein could extend as low as 40% oxygen concentration; but Richard provides no teaching concerning how such a system would be implemented, the effect on patients, etc., and no system corresponding to this disclosure of Richard is known in the art. Similarly, U.S. Pat. No. 10,799,663 to Oddo et al. allegedly discloses, again in a single mention, oxygen concentrators delivering enriched oxygen in amounts as low as exceeding the oxygen concentration in atmospheric air, which is 21%, but, again, provides no details concerning how such a system might work, and it is believed that such extremely low oxygen concentration airflows would not be effective for users, such as COPD patients. Canadian Pat. No. CA2810669 to Wilkinson et al. similarly discloses oxygen-enriched air in amounts as low as 50%, also without mention of how such a system may function and how it may be effective for COPD patients.

*Characterization and Feasibility of a Portable Oxygen Concentrator for use with a Mass Casualty Ventilator*, a thesis by Paul Robert Williams, December 2013, suggests that such high purity oxygen may not be required in all instances, and that one might consider reducing compressor capacity, or modifying compressor settings to provide only a level of purity needed to maintain oxygen levels in the patient. The Williams Thesis mentions that one could increase flow rate, produce more oxygen, but deliver at a lower concentration of oxygen (<90%), and contemplates modifications of an existing system(s) from pulse to continuous flow. Most of this thesis focuses on adapting an existing POC and combining with a mass casualty ventilator in preparation for pandemic emergencies, and does not suggest how, if at all, the suggested machine could function as a long-term solution for chronically ill COPD patients. More than seven years after its publication the Williams' Thesis does not appear to have had an impact on how commercial POCs are designed or operate. The work in the Williams' Thesis also does not appear to have been the basis of any related or further patent or literature disclosures, reflecting a lack of motivation in the art to adopt or modify this work.

U.S. Pat. No. 10,583,265 to Whitcher et al. discloses POCs with both pulse and continuous delivery where the system can measure the oxygen flow rate, pressure, and temperature, and based on the measurement, control the frequency and/or duration of the opening of the oxygen delivery valve. Similarly, Japanese Pat. Appl. Pub. No. JP2008517638 to Bosinski et al. touches on the number of molecules of oxygen delivered per dose/inhalation, and how it is affected by the pressure and temperature of the gas. Wilkinson, mentioned above, also discloses the number of oxygen molecules in a given volume of air being increased by removal of heat from the compressed air.

As of today, limited or no options exist for treating patients with especially advanced breathing difficulty, such as occurs in COPD, with enough oxygen to provide a therapeutic effect, while doing so in a manner that is efficient enough to extend the efficiency and, thus, e.g., the battery life of most POCs (e.g., beyond 1-1.5 days). Clearly, given the significant interest in the art in such improvements, achieving practical systems that can safely and effectively deliver oxygen that patients, such as COPD patients, require, while reducing the energy expenditure of such units, will require the application of inventive ingenuity.

Construction, Definitions, & Abbreviations

Terms such as "here" and "herein" means "in this disclosure." Except where otherwise specified, any part of this disclosure as being applicable to any other suitable part of the disclosure. The term "elsewhere" also typically means "elsewhere in this disclosure."

There are several aspects of the invention here. The term "aspects," unless otherwise indicated, refers to "aspects of this invention." The "invention" encompasses all aspects herein, individually & collectively (methods and devices/systems/compositions). The abbreviation "AOTI" means "aspect(s) of the invention."

The intended audience for this disclosure ("readers") are persons having ordinary skill in the art in the practice of the technologies discussed herein ("skilled persons"). Technological aspects of elements/steps provided here are sometimes omitted in view of the knowledge of readers. The terms "technology" and "art" here refer to the knowledge of such skilled persons. In cases, citation of reference(s) adaptable to AOTI are included here. All such patent documents and other publications are hereby incorporated by reference to the same extent as if each reference were individually and specifically indicated to be incorporated by reference and were set forth in its entirety herein. The disclosure of such references can be combinable with this disclosure; however, incorporation of patent documents is limited to the technical disclosure thereof and does not reflect on validity, patentability, or enforceability thereof. Moreover, in the event of any conflict between this disclosure and the teachings of such documents, the content of this disclosure will control with respect to properly understanding the various aspects of the invention. Readers will also understand that some features of some cited references are not applicable to AOTI.

"Uncontradicted" means not contradicted explicitly, clearly by context, or by inoperability/impossibility. "Contradicted" has a corresponding meaning.

Heading(s) here (e.g., "CONSTRUCTION, DEFINITIONS, . . . ") are used for convenience only. Except where clearly otherwise indicated, aspects of the invention described in part or entirely under a heading can apply to other aspects described in other sections of this disclosure.

The inclusion of "(s)" after an element indicates that greater than one (≥1) of such an element can be present, performed, and the like. E.g., "an element comprising component(s)" means an element including one component and a composition comprising two or more components, each part of the statement being separate aspects and collectively representing a higher level (genus) aspect. For conciseness symbols also are used herein wherever clear. E.g., "&" is used for "and" and "~" is used for "about," and ">" means "greater than 1." The term "i.a." (sometimes presented as "ia") means "inter alia" or "among other things." "Also known as" is abbreviated "aka," and refers both to the knowledge of skilled persons as well as any synonymous description of elements here.

Ranges here concisely refer to values within the range within an order of magnitude of the smallest endpoint. E.g., readers should interpret "1-2" as implicitly disclosing each of 1.0, 1.1, 1.2, 1.3, 1.4, 1.5, 1.6, 1.7, 1.8, 1.9, and 2.0 and "5-20" as implicitly disclosing each of 5, 5.1, 5.2, . . . , 6, 6.1, 6.2, . . . 19, 19.1, . . . 19.9, and 20). Ranges here include end points, regardless of how the range is described (e.g., a range "between" 1 and 5 will include 1 and 5 in addition to 2, 2.1, . . . , 3, 3.1, . . . , 4, 4.1, . . . and 4.9). Uncontradicted, applying a modifier to 1 or 2 endpoints does not change the range's value (e.g., "about 10-20" means "about 10-about 20").

Terms of approximation, e.g., "about" or "approximately" (or ~) here refer to a range of closely related values, a value that is difficult/impossible to precisely measure, or both, and, thus, include the precise value as an aspect of the disclosure (e.g., "10" is an aspect of a disclosure of "about 10"). Similarly, it will be understood that precise values provided herein support approximately similar ranges unless contradicted. The scope of an approximate value depends on the value, context, and technology (e.g., criticality or operability, other evidence, statistical significance, or general understanding). In the absence of guidance here or in the art, terms of approximation such as "about" or "approximately" mean +/−10% of the indicated value(s).

Uncontradicted, each member of each list of elements reflects an independent AOTI (often having distinct/nonobvious properties with respect to the other listed elements/aspects or features).

Uncontradicted, "or" means "and/or" here. The occasional explicit use of "and/or" herein has no effect on this interpretation of "or." Uncontradicted, the scope of "or" meaning "and/or" in a phrase such as "A, B, and/or C" or "A, B, and C" implicitly supports each of the following embodiments: A, B, and C; A, B, or C; A or C; A or B; B or C; A and C; A and B; B and C; A (alone); B (alone); and C (alone).

Uncontradicted, "a," "an," "the," and similar referents indicate both the singular and the plural of any associated element. Uncontradicted, terms presented in the singular implicitly convey the plural and vice versa here (e.g., a passage referring to use of an "element" implicitly discloses use of corresponding "elements," and vice versa). Uncontradicted, "also" means "also or alternatively" (abbreviated "AOA"). The "/" symbol is sometimes used to indicate an "or" relationship between elements (e.g., "A/B" means "A or B"). Terms like "combination," "and combinations," or "or any combinations" regarding listed elements mean "a combination of any or all of such elements"

The term "some" used in connection with a collection of elements means "two or more" & in respect of a part of a whole means "at least 5%" (i.e., ≥5%). "Significant" and "significantly" means results/characteristics that are statistically significant using an appropriate test in the given context (e.g., p≤0.05/0.01). "Detectable" means measurably present/different. The modifying abbreviation "DOS" means "detectable or significant" or "detectably or significantly."

Uncontradicted, terms such as "including" "containing," and "having" mean "including, but not limited to," "including, without limitation," or "comprising." "Comprising" means including any detectable amount of a feature or including any detectable performance of a step. An aspect described as "comprising" or "including" a step/element can include that step/feature alone or in combination with any other associated element.

Uncontradicted, a description of an aspect "comprising" or "including" an element (step/feature) simultaneously implicitly discloses corresponding AOTIs that (1) consists of the feature, (2) consists essentially of the feature, (3) substantially consists of ("SCO") the feature (or "substantially is" or is/are "substantially only" the step/element), (4) generally consists of ("GCO") the feature (or is "generally adapted" to, is "generally composed" of, "generally is," "generally only" is/are, "generally are," the feature), (5) predominately comprises ("PC") the feature ("mostly" or "primarily" comprises) the step/element, (6) materially comprises the step/element, and (7) appreciably comprises ("AC") the step/element.

Terms such as "consists of" (abbreviated "CO") & "consists essentially of" ("CEO") are given their ordinary meaning here (i.e., limited to the feature, within bounds of detection and practicality in the first case and not materially affecting the basic and novel characteristics of the referenced feature in the latter). Skilled persons either know the "basic and novel characteristics" or CEO should be treated the same as SCO. Terms such as "only" or "all" are sometimes used in place of "consists of," and "essentially" is sometimes used in place of "consists essentially of."

"Substantially consists of" ("SCO") means ≥95% of the referenced collected/part is made up of the referenced feature and "substantially associated" means that at least 95% of a referenced item are associated with a second referenced item. "Substantially all" means at least 95% of the referenced items/steps meet(s) the indicated condition.

Terms such as "generally consists of" (abbreviated "GCO"), "generally is," "generally are," "generally all," "generally," "generally is composed of," and "generally," mean the referenced feature makes up 75% of the related whole. Similarly, "generally associated" means 75% of an element is associated with a 2nd element (e.g., 75% of 1 agent is associated with a 2nd agent). "Generally most" and "generally all" mean 75% of the referenced items/steps meet the indicated condition.

"Predominately comprises" (abbreviated "PC") means 50% of a collection/thing is composed of the referenced feature and "predominately associated" is construed similarly.

The acronym "OSMGASAOA" in connection with an element means "one, some, most (i.e., PC), generally all (i.e., GCO), substantially all (i.e., SCO), or all (i.e., CO)," each of which is implicitly disclosed as a separate facet of the described aspect (i.e., part of the genus). The abbreviation "MGASAOA" similarly means "PC, GCO, SCO or CO" and "SMGASAOA" means "some, most, generally all, substantially all, or all." the acronym "GASAOA" similarly means "generally, substantially only, or only."

"Materially comprises" ("MC") means 10% of a collection/thing is made up of a referenced feature. "Materially associated" is similarly construed. "In material part" means 10%) of referenced items/steps. "Appreciably comprises" (abbreviated "AC") means at least 1% of a collection or item is composed of the referenced element/component. The phrase "appreciably associated" means that 1% of an element is associated with another referenced element.

Changes to tense or presentation of terms (e.g., using "comprises predominately" in place of "predominately comprises") do not modify the meaning of the related phrase unless indicated.

Terms such as "operatively associated with" or "operatively linked" means an element that operates in association with another element (operates in relation to an associated element), causes the operation of a $2^{nd}$ associated element (or vice versa), or promotes/enhances the operation of such a $2^{nd}$ element.

Unless "means for" or "step for" are used here, no element should be given a "means-plus-function" construction. Terms like "configured to" or "adapted to" are not "means-plus-function" terms, but, rather, refer to features configured, designed, selected, or otherwise adapted to achieve a performance, characteristic, property, or the like using this disclosure and technology.

Uncontradicted, methods described here be performed in any suitable order. Uncontradicted, devices/compositions can be assembled/generated in any suitable manner by any suitable method. Uncontradicted, any combination of elements, steps, components, or features of aspects and apparent variations thereof, are AOIT.

Numerous examples of aspects are provided in this disclosure to illuminate AOTI. The breadth and scope of the invention should not be limited by any of the exemplary embodiments. No language in the specification should be construed as indicating any element is essential to the practice of the invention unless such a requirement is explicitly stated.

The following table lists abbreviations of technical elements that are frequently used in this disclosure and provides a description of the general meaning thereof which may be supplemented by knowledge of skilled persons.

TABLE 1

Abbreviations

| Abbreviation | Term | Brief Description |
|---|---|---|
| ARDS | Acute respiratory distress syndrome | Respiratory failure characterized by widespread lung inflammation |
| BiPAP | Bilevel Positive Airway Pressure | A machine like a CPAP, but with separate pressure settings for inhalation and exhalation |
| COPD | Chronic obstructive pulmonary disease | A group of chronic lung conditions, that cause obstructed or blocked airways |
| CPAP | Continuous Positive Airway Pressure | Machine that increases air pressure in the throat to assist patients with obstructive sleep apnea breathe more easily during sleep |
| EOA | Enriched oxygen airflow | Airflow that has a higher concentration of oxygen than is found in ambient air |
| HEOA | Highly enriched oxygen airflow | Airflow that has an oxygen concentration of at least about 90% |
| IEOA | Intensively enriched oxygen airflow | Airflow that has an oxygen concentration of about 60-90% |
| LTOT | Long-Term Oxygen Therapy | Treatment used to improve survival in COPD patients with chronic respiratory failure |
| MEOA | Moderately enriched oxygen airflow | Airflow that has an oxygen concentration of about between 33-48% |
| NAM | Nitrogen adsorption media | Media that removes nitrogen from ambient air to yield an enriched oxygen airflow |
| PC | Programmable controller | A controller that contains programmable stored computer readable instructions and a processor for executing such instructions and means for controlling operation of system component(s) |
| PGGS | Pressure gradient generating system | System for generating a pressure gradient to apply to the nitrogen adsorption media |
| POC | Portable oxygen concentrator | A lightweight, battery-powered device for providing supplemental oxygen to a patient |
| PODI | Patient oxygen delivery interface | A device that facilitates administration of an airflow to a patient |

SUMMARY OF THE INVENTION

Certain aspects of the invention described in this Summary refer to aspects described in other paragraphs, incorporating all of the elements of any such one or more referenced paragraphs. To facilitate such referencing, a paragraph number is provided at the end of each paragraph in this section.

The invention described here provides new methods for more efficiently delivering surprisingly effective amounts of oxygen to a mammalian subject, such as a person experiencing hypoxemia or other related disease or condition, such as a COPD patient, e.g., a COPD patient having low blood oxygen saturation as compared to typical normal levels. The methods of the invention typically comprise administration of one or more enriched oxygen airflows that is/are not a highly enriched oxygen airflow or an intensively enriched oxygen airflow, but that nonetheless deliver enough oxygen to the subject to treat a disease or condition, prevent the progression or occurrence of a disease/condition, or both (Summary paragraph 2).

In one aspect, the method comprises providing a human patient, such as a COPD patient or chronic hypoxemia patient, with a portable oxygen concentrator, and (I) delivering to the patient one or more enriched oxygen airflows comprising an oxygen concentration of less than 50%, such as about 33-48% (a MEOA), e.g., an MEOA comprising about 35-45%, or such as about 37-40% oxygen, in association with most, at least generally all, or at least substantially all breaths of such patient over a sustained period (e.g., at least 1, at least 3, at least 6, at least 12, at least 18, at least 24, or at least 30 months) and (II) delivering the enriched oxygen airflow to the patient, in an average amount per patient breath (inspiration) that is about the same as the amount of oxygen delivered in a typical portable oxygen concentrator (POC) that delivers a highly enriched oxygen airflow (HEOA) or statistically similar to the amount of oxygen delivered in a typical POC delivering a HEOA. In one aspect, such a method further includes monitoring one or more conditions in the patient, such as breathing of the patient through a patient oxygen delivery interface ("PODI") (e.g., a nasal canula), as detected by one or more sensors or techniques, and changing the oxygen concentration of the enriched oxygen airflow ("EOA") delivered to the patient based on such conditions from a MEOA to a HEOA or IEOA, or vice versa based on such conditions. In aspects, such a determination is made by a programmable controller that controls operational component(s) of an enriched oxygen airflow delivery system(s) that generates the EOA, delivers the EOA(s) to the patient, or both (Summary paragraph 3).

In one aspect, the invention provides a method that comprises providing a human patient, such as a COPD patient or chronic hypoxemia patient, with a POC that selectively delivers one or more enriched oxygen airflows to the patient and that comprises (1) a pressure gradient generating system ("PGGS"), (2) at least one nitrogen adsorption media ("NAM") that generates an enriched oxygen airflow when exposed to air and acted on by a sufficient pressure gradient and that is selectively isolated from the environment by at least one air enrichment area separator, (3) an enriched oxygen airflow outlet that is fluidly connected to a flow line and a patient oxygen delivery interface (such as a nasal cannula), (4) a programmable controller ("PC") comprising stored computer readable instructions and a processor for executing such instructions and that in operation determines (I) the volume of the airflow delivered to the patient, (II) the oxygen concentration of the airflow, and (III) whether to deliver enriched oxygen airflow to a patient via continuous delivery or pulse delivery, and (5) one or more sensors configured to detect changes in the patient, such as changes in patient oxygen intake (e.g., at least one breath/breathing rate sensor), where the delivery of the enriched oxygen airflow comprises (I) generating a moderately enriched oxygen airflow (MEOA) comprising an oxygen concentration of less than 50%, such as 33-48%, such as 35-45%, or such as 37-40%, and (II) pulse delivering the MEOA to the patient, in an effective amount per pulse (or per average pulse or generally all pulses) (e.g., about 80-about 240 mL of the moderately enriched airflow per inspiration, such as about 90-230 mL, such as about 100-220 mL, such as about 110-210 mL, such as about 120-200 mL, such as about 130-190 mL, such as about 140-180 mL, or such as 150-170 mL), such that the average millimoles (mmol) of oxygen delivered to the patient per inspiration is about the same as or statistically similar to the amount of millimoles of oxygen delivered to the patient per inspiration of a highly enriched oxygen airflow having an oxygen concentration of at least about 90%. Such a method can further include the steps of automatically changing between continuous delivery and pulse delivery based on one or more patient characteristics detected by the system (when the controller determines that one or more aspects of the patient's breathing exceeds one or more pre-programmed thresholds), such as the patient's breathing rate, breathing volume, blood oxygen level, or other characteristic(s) detected by sensor(s). Monitoring of characteristics in a patient can comprise, e.g., monitoring breathing of the patient through the patient oxygen delivery interface ("PODI"), such as a nasal enriched oxygen airflow cannula. In AOTI, a change from pulse to continuous delivery is associated with a change in delivery of a MEOA to a HEOA/IEOA (Summary paragraph 4).

In a further aspect, the invention provides a method such as that described in Summary paragraph 3 or Summary paragraph 4, wherein in SMGAOA cases of continuous delivery the POC delivers about 240-640 mL of an IEOA or HEOA to the patient, e.g., about 260-620 mL, e.g., about 280-600 mL, such as about 300-580 mL, such as about 320-560 mL, such as about 340-540 mL, e.g., about 350-550 mL, about 350-530 mL, about 350-520 mL, such as about 360-520 mL, such as about 380-500 mL, e.g., about 390-470 mL, such as about 400-480 mL of either an intensively enriched oxygen airflow or highly enriched oxygen airflow (Summary paragraph 5).

In another aspect, the invention provides methods such as those described in Summary paragraph 3, wherein the POC switches from pulse delivery to continuous delivery or vice versa at least once per day (e.g., per 24-hour interval) on average during a treatment period of ≥1, ≥3, ≥6, ≥12, or ≥18 months (Summary paragraph 6).

In another aspect, the invention provides a method such that as described in Summary paragraphs 3-6, further comprising automatically changing the POC's airflow from an MEOA to an intensively enriched oxygen airflow or highly enriched oxygen airflow based on the detection of one of more conditions comprising one or more breath/breathing rate conditions in the patient. In aspects, the change is made automatically by a PC in response to signals from one or more sensors meeting or exceeding threshold(s) associated with physiological condition(s) (Summary paragraph 7).

In another aspect, the invention provides a method such as that is described in Summary paragraphs 3-7, wherein the method further comprises automatically changing the airflow from an intensively enriched oxygen airflow or highly enriched oxygen airflow to a moderately enriched oxygen airflow based on the detection of one or more conditions comprising one or more breath/breathing rate conditions in the patient (Summary paragraph 8).

In another aspect, the invention provides a method such as any of the methods described in Summary paragraphs 3-8, wherein the average rate of enriched airflow to the patient in continuous delivery, pulse delivery, or both, is at least about 3.3 L/minute. In aspects, the average rate of enriched airflow to the patient in continuous delivery, pulse delivery, or both, is greater than about 3.6 L/minute (Summary paragraph 9).

In another aspect, the invention provides a method such as any method as described in any of Summary paragraphs 3-9, wherein the average oxygen intake per patient inspiration is about 0.05 mmol-about 0.5 mmol oxygen (Summary paragraph 10).

In another aspect, the invention provides methods such as the methods described in any part of Summary paragraphs 3-10, wherein the method comprises operating the pressure gradient system at least about 33% longer, opening the air enrichment area separator at least about 33% longer, or both, as compared to the default operating parameters of a commercially available POC, such as an Inogen One® G3, Inogen One® G4, or Inogen One® G5 POC (Summary paragraph 11).

In a further aspect, the invention provides a method such as that described in any part of Summary paragraphs 3-11, wherein the method comprises applying a pressure gradient comprising a maximum pressure of about 10-about 30 PSI to the nitrogen adsorption media Summary paragraph 12).

In a further aspect, the invention provides a method such as any method described in any part of Summary paragraphs 3-12, wherein the delivery of oxygen consumes an average of between about 30-90 Watts of energy, such as between about 30-80, 30-70, or 30-60 Watts (e.g., 40-90, 45-90, 50-90, 40-80, 45-80, 35-75, 45-75, or 55-75 Watts) Summary paragraph 13).

In a further aspect, the invention provides a method such as any method described in any part of Summary paragraphs 3-13, wherein the concentration of oxygen in MEOA(s) delivered to the patient in the method is about 40%, such as 38-42%, e.g., 39-41%, or 39.5-40.5%, and the average volume of moderately enriched airflow delivered per inspiration is between about 40 mL to about 520 mL, such as about 90-470 mL, such as about 140-420 mL, such as about 190-370 mL, or such as about 240-320 mL (Summary paragraph 14).

In a further aspect, the invention provides a method such as any method described in any parts of Summary paragraphs 3-14, wherein the average volume of moderately enriched airflow delivered per inspiration is between about 150-350 mL, such as about 170-330 mL, such as about 190-310 mL, such as about 210-290 mL, or such as about 230-270 mL (Summary paragraph 15).

In another aspect the invention provides a method such as that described in any part of Summary paragraphs 3-15, wherein the average volume of moderately enriched airflow delivered per inspiration thereof is at least about 200 mL. In aspects, the average volume of MEOA(s) delivered per inspiration in one or more modes of POC operation is ≥~300 mL (Summary paragraph 16).

In another aspect the invention provides a method such as that described in any part of Summary paragraphs 3-16, wherein the patient has an average blood oxygen saturation of lower than about 93% or 92%, such as about 88%-92%, at the initiation of the method (Summary paragraph 17).

In a further aspect, the invention provides a method such as any method described in any part of Summary paragraphs 3-17, wherein the method comprises testing the patient for tolerance of moderately enriched oxygen airflow under supervision of a healthcare provider before allowing the patient to self-manage the portable oxygen concentrator (Summary paragraph 18).

In a further aspect, the invention provides a method such as any method described in any part of Summary paragraphs 3-18, wherein the portable oxygen concentrator generates an average of less than ~50, ~40, ~35, or less than ~30 decibels of noise during most, generally all, substantially all, or all periods of operation (Summary paragraph 19).

In a further aspect, the invention provides a method such as that described in any part of Summary paragraphs 3-19, wherein the method is performed for a period of at least about 6 months (e.g., ≥~30 months) (Summary paragraph 20).

In a further aspect, the invention provides a method such as that described in any part of Summary paragraphs 3-20, wherein airflow(s) delivered to the patient consists essentially of oxygen enriched air (e.g., in being free of active pharmaceutical agent(s), gasses not found in normal atmospheric air, additional moisture, or a combination thereof). In aspects, application of the method is the primary method employed to relieve temporary breathing conditions in the subject/patient (Summary paragraph 21).

In aspects, any of the above-described methods comprises a step of monitoring the patient for an initial testing period to assess the suitability/effectiveness of delivering MEOA(s) to the patient for some, most, generally all, or all the oxygen delivery period of each day, typically over a treatment period (e.g., ≥2 days, ≥4 days, ≥5 days, ≥7 days, ≥2 weeks, or ≥1 month). In aspects, such tests are conducted under the supervision of a health care provider prior to permitting the patient to self-manage the POC/delivery of oxygen (Summary paragraph 22).

The invention also provides new systems capable of delivering an effective and efficient moderately enriched oxygen airflow ("MEOA") and that can perform any of the above-described methods in this Section (Summary paragraph 23).

In one such exemplary aspect, the invention provides a system comprising a portable oxygen concentrator comprising (a) a pressure gradient generating system, (b) at least one nitrogen adsorption media configured to generate an enriched oxygen airflow when exposed to air and acted on by a sufficient pressure gradient and that is selectively isolated from the environment by at least one air enrichment area separator, (c) an enriched oxygen airflow outlet that is fluidly connected to a flow line and a patient oxygen delivery interface, (d) a programmable controller comprising stored computer readable instructions and a processor to determine (1) the volume of the airflow delivered to the patient, (2) the oxygen concentration of the airflow, and (3) to cause delivery of enriched oxygen airflow to a patient either via continuous or pulse delivery, and (e) one or more sensors configured to detect changes in patient oxygen intake, such as at least one breath/breathing rate sensor, wherein in operation (1) the controller controls the operation and operating conditions of the pressure gradient generating system, the at least one air enrichment area separator, the enriched oxygen airflow outlet, and the oxygen delivery interface, (2) the one or more sensors are configured to monitor breathing of the patient through the oxygen delivery interface and determine whether one or more aspects of a user's breathing exceeds one or more pre-programmed thresholds, (3) the controller causes the delivery of enriched oxygen to change from a pulse delivery to a continuous delivery and back again based on whether the breathing of the patient exceeds the one or more pre-programmed thresholds, and (4) in pulse delivery the system generates and delivers a moderately enriched oxygen airflow comprising between 33-48% oxygen and delivers the moderately enriched oxygen airflow in pulses of about 80-about 240 mL. In aspects, the POC is configured to deliver to the patient about 240-640 mL of intensively enriched airflow wherein the intensively enriched oxygen airflow comprises 60-90% oxygen, a highly enriched oxygen airflow (comprising ≥~90% oxygen), or both, typically under continuous flow conditions (Summary paragraph 24).

In one aspect, the invention provides a system such as that described in Summary paragraph 24, wherein the POC also is configured to switch from pulse delivery to continuous delivery, from continuous delivery to pulse delivery, or any combination thereof, at least once per day (e.g., per 24 hour interval) on average, over a period of treatment (e.g., ≥~1 month, ≥~3 months, ≥~6 months, or ≥~12 months). In one aspect, the POC also (i.e., also or alternatively) is configured to change the airflow from the moderately enriched oxygen airflow to the intensively enriched airflow/highly enriched oxygen airflow, from an intensively enriched oxygen airflow (or HEOA) to a moderately enriched oxygen airflow, or any combination thereof, based on the detection of one of more conditions in the patient/subject, such as rate of breathing, determined by sensor(s) of the system or that are operatively linked to the system (e.g., by a shared electronic medical record). In one aspect, the POC is configured to deliver an average rate of enriched airflow in continuous delivery, pulse delivery, or both, of at least about 3.3 L/minute or at least about 3.6 L/minute. In aspects, the system is configured to deliver an average volume of about 0.05 mmol to about 0.5 mmol of moderately enriched airflow, per inspiration of the patient. In aspects, the system is configured/adapted such that the pressure gradient applied to the nitrogen adsorption media comprises a maximum pressure of about 15-25 PSI. In aspects, operation of such a system in one or more modes of operation (or all modes of operation), on average, mostly, generally, substantially, or entirely consumes an average of about 30-90, such as 30-60 Watts of energy. In aspects, the system is configured to deliver an average volume of between about 150-350 mL (e.g., about 200 mL) of moderately enriched oxygen airflow per typical inspiration (e.g., as determined by clinical testing, modeling, consumer testing, or combination), in at least one mode, if not all modes of operation. A "mode" in this respect can be considered a setting in which the POC delivers a defined type of enriched oxygen airflow, such as one particular type of an enriched oxygen airflow, such as only MEOA (or separately only HEOA/IEOA), provided that the mode can include variations and transitions, such that it is possible to describe a mode as generally, substantially only, or essentially being associated with the referenced type of enriched oxygen airflow. In aspects, pulse delivery comprises more than one pulse delivery mode, each pulse delivery mode comprising different oxygen concentrations, different volumes of enriched oxygen airflow, or both. In other aspects, systems are configured to deliver an average volume of at least about 300 mL of moderately enriched airflow per inspiration of a typical patient in at least one mode (e.g., when delivering a moderately oxygen enriched airflow). In aspects, such a system can comprise a pressure gradient that operates on average, generally, substantially, or only at least about 33% longer; on average, generally, substantially, or only opening the air enrichment area separator at least about 33% longer; or both, as compared to the default operating parameters of a commercially available POC, such as an Inogen G3, Inogen G4, or Inogen One® G5 POC (Summary paragraph 25).

BRIEF DESCRIPTION OF THE DRAWINGS/FIGURES

DETAILED DESCRIPTION OF THE INVENTION

Figure 1:
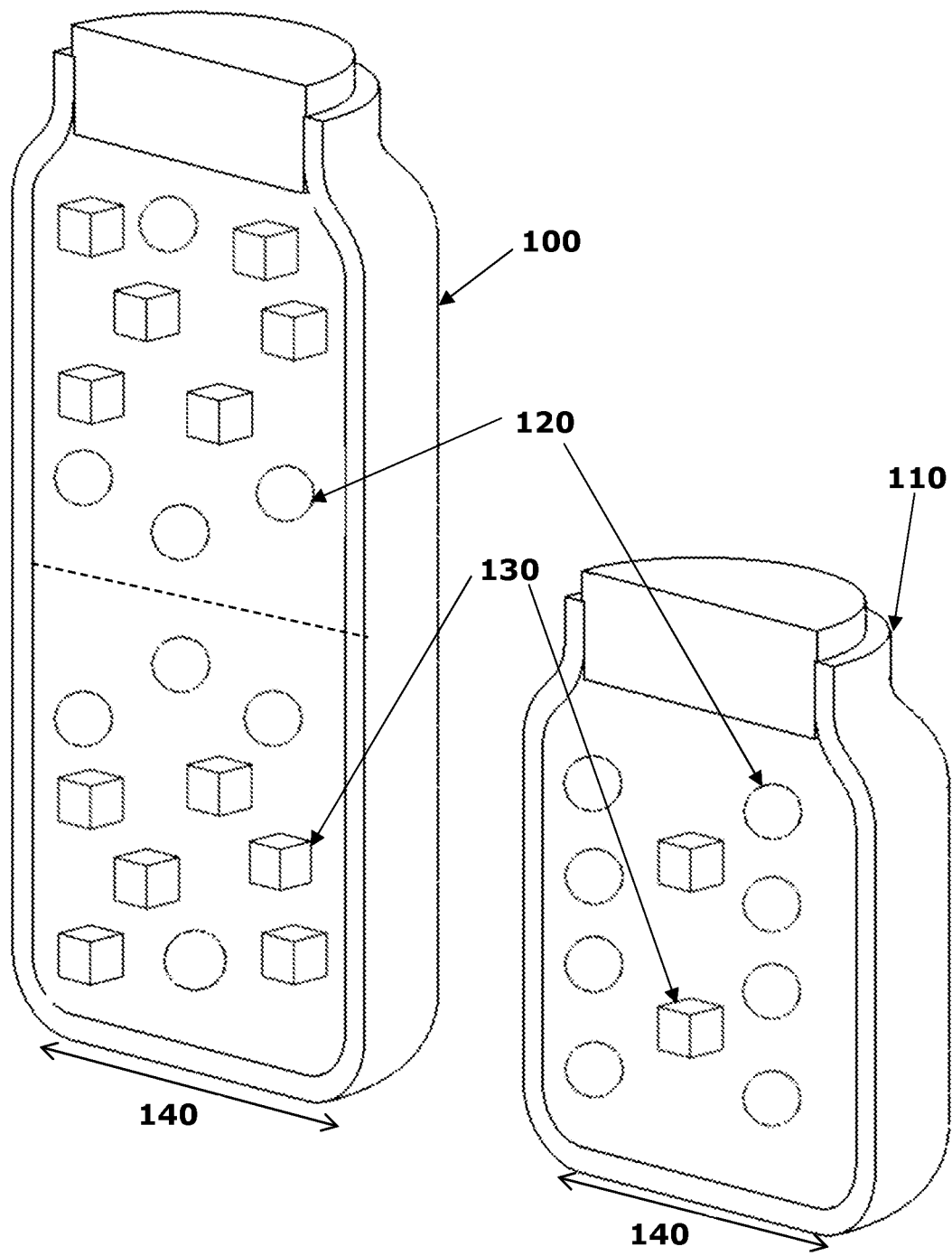
FIG. 1 is an abstract representation comparing the molar ratio of enriched oxygen molecules to total air volume delivered by a portable oxygen concentrator of the present invention compared to that of portable oxygen concentrators described in the prior art (delivering 80% enriched oxygen).

Described herein are new methods of, and systems for, delivering oxygen to subjects (e.g., patients with a disease/condition associated with the need for enhanced oxygen intake for treatment or prevention of such a disease/condition). Methods and systems of the invention are characterized by the generation and delivery of moderately enriched oxygen airflow(s) to the subject/patient during period(s) of the treatment, under certain conditions in the patient, or both. In aspects, a MEOA is delivered consistently to the subject/patient in the method/system. In aspects, the method comprises switching, and the system is configured to switch, between mode(s) comprising delivery of MEOA(s) and mode(s) comprising delivery of IEOA(s), HEOA(s), or both, and back again based on one or more conditions, parameters, or a combination of both.

In one exemplary aspect, the invention provides a method of, and/or in aspects a system for, assisting breathing in a subject, such as a patient suffering from chronic obstructive pulmonary disease (COPD) (e.g., a COPD patient having a low blood oxygen saturation as described herein or in the art). In aspects, the method/system comprises providing the patient with a POC comprising (1) a pressure gradient generating system, (2) at least one nitrogen adsorption media, (3) an enriched oxygen airflow outlet that is fluidly connected to a flow line and a patient oxygen delivery interface (such as a nasal cannula), (4) a programmable controller comprising stored computer readable instructions and a processor for executing such instructions and that in operation determines (I) the volume of the airflow delivered to the patient, (II) the oxygen concentration of the airflow, and (III) whether to deliver enriched oxygen airflow to a patient via continuous delivery or pulse delivery, and (5) sensor(s) that detect change(s) in the patient related to oxygen intake/concentration in the patient. In aspects, the method further comprises delivering an enriched oxygen airflow to the patient for a sustained period (chronically) (e.g., for a period of ≥~1 month, ≥~3 months, ≥~6 months, ≥~12 months, or ≥~18 months), by (1) generating a moderately enriched oxygen airflow comprising an oxygen concentration of ~33-48% (e.g., ~35-45%, ~34-46%, ~38-48%, ~38-46%, or ~38-44%) during one or more periods of treatment. In aspects, the method comprises pulse delivering to the patient about 80-about 240 mL of an airflow selected from one or more moderately enriched airflows per inspiration. In aspects, the average millimoles of oxygen delivered to the patient per inspiration is statistically similar to the average amount of millimoles of oxygen delivered to a similar patient or class of patients per inspiration of a highly enriched oxygen airflow ("HEOA") (e.g., comprising ≥87%, 88%, or 90% oxygen). In aspects, the method comprises monitoring one or more patient conditions relating to oxygen levels, oxygen intake, or an oxygen level/intake-related physiological parameter or health condition, and modifying the oxygen delivery volume, concentration, or both, to the patient based on the change in parameter(s). In one exemplary aspect, the parameter comprises oxygen concentration in the patient, breathing rate, breathing volume, or a combination thereof, and the method comprises automatically changing between continuous delivery and pulse delivery of enriched oxygen airflow(s) based on one or more parameter(s) detected by sensor(s) operatively associated with the POC reaching or exceeding one or more pre-programmed thresholds. In aspects, such a change in airflow occurs only upon validation of the meeting or exceeding of such threshold(s)/standard(s), such as when ≥2, ≥3, or ≥4 parameters are met/exceeded, a parameter is met or exceeded by ≥2 different sensor(s), a parameter is met/exceeded in 2 different readings, or a combination thereof.

Various features of the inventive methods/systems are described in detail in the following sections, but readers will understand that this is for convenience only and any aspect described in connection with one element/step or characteristic/aspect can be combined with any other aspect, facet, or characteristic of the invention unless contradicted.

Subjects/Patients/Users and Associated Persons (e.g., HCPs)

Methods/systems of the invention can be adapted/applied to any suitable mammalian subject, including companion animals, livestock animals, laboratory animals, zoological animals, and humans. In aspects, the subject of a method or the subject for which a system is adapted to be applied to is a human patient, such as a human patient having or identified as being at risk of developing a disease/condition associated with low oxygen concentration, low oxygen intake, or both. In an exemplary aspect, the subject has blood oxygen levels which are reduced compared to normal human levels in one or more contexts, such as at rest, or, for example, such as an oxygen saturation level ($SpO_2$ level) of less than 95%, such as less than 93%, such as less than 92%, less than 91%, or less than 90%. In aspects, the subject is a patient diagnosed with a condition that requires the assistance of an external oxygen device to replenish oxygen levels. In aspects, the subject is an individual suffering from respiratory problems or diseases affecting their lung function or capacity. In aspects, the subject is a person diagnosed as suffering from one or more of COPD, asthma, sleep apnea, cystic fibrosis, ARDS, or other lung/lung-related disease or condition. In aspects, the subject is a person diagnosed with COPD. In aspects, the subject is a person diagnosed with such condition(s) and having one or more related co-existing health conditions, such as arthritis, congestive heart failure, diabetes, allergic conditions, coronary heart disease, stroke, or asthma, or other condition(s) which further impact the subject's breathing, oxygen retention, or strength, mobility, or stamina. In aspects, the patient is a patient that has been diagnosed/approved for (prescribed) or has a condition typically associated with or requiring an oxygen delivery treatment protocol that would be recognized as a long-term oxygen therapy (LTOT).

POC and Enriched Oxygen Airflow Delivery

The POC component can be any suitable type of POC. Typically, the POC will be a relatively small, portable unit (e.g., having a weight of about 1.5-25 pounds, such as about 1.5-15 or 2-20 pounds, often about 2.5-10 pounds, 2-10 pounds, 2-8 pounds, 3-9 pounds, or 4-10 pounds). In aspects, the POC is about 2.5-15 inches in most or all dimensions (width, depth/length, and tallness/height). In aspects, 1, 2, or 3 of the dimensions are between ~1-12, ~1.5-10.5, ~2-12, ~3-12, ~3-9, ~2-10, or ~4-9 inches. The POC can be any suitable POC that has the capability to deliver the same amount of oxygen per inspiration at a significantly lower overall oxygen concentration (e.g., an oxygen concentration of 33-48%, such as 35-45%) than administered by typical commercial units, such as Inogen One® G Series POC units or other units on the market (i.e., an oxygen concentration of 90-95%).

In one aspect, the POC is an "enhanced POC." An enhanced POC is a POC that originally was produced without the ability to deliver an MEOA, without the ability to switch between an MEOA delivery mode and other modes, or both, but which is modified to be able to deliver an MEOA to a patient, to switch between delivery of MEOA(s) and HEOA(s)/IEOA(s), or both. For example, in one exemplary aspect, an enhanced POC is obtained based on the modification of an Inogen One® G series POC that lacked such capabilities in original production specifications, when made available for sale, or sold, or both, and that is adapted through modification of, i.a., the POC's operating system to be able to perform the function(s) of the methods/systems of the invention. In aspects, the enhanced POC comprises the addition of one or more user accessible setting(s) not originally contained/programmed in the POC. E.g., in a POC initially having six different modes of operation, an enhanced POC state can comprise a 7th setting, or $7^{th}$ and $8^{th}$ settings, or $7^{th}$, $8^{th}$, and $9^{th}$ settings, etc., reflecting modes in which an MEOA is delivered to the patient, typically at volumes higher than initial settings. In one aspect, the method provides a method of modifying an existing POC having an MEOA delivery functionality comprising changing the operating system of the POC to change the operational characteristics of oxygen enrichment (time of operation, pressure of operation, or both, or conditions/timing of contact with the NAM), oxygen airflow characteristics (typically increasing volume of oxygen delivered), or a combination thereof. In aspects, an enhanced POC also comprises a continuous delivery or pulse delivery mode where no such type of mode was present in the POC prior to enhancement. In an aspect, the invention provides a method of enhancing the functionality of a POC comprising providing the POC with the ability to apply MEOA(s) to a subject under conditions to deliver a statistically similar or approximately the same amount of oxygen per average patient inspiration as delivered by the POC using a IEOA or HEOA under the delivery conditions used in current on-market POCs, such as the Inogen G Series POCs. In aspects, the enhancement of a POC comprises providing the POC with a controller that automatically changes from mode(s) to other mode(s), wherein at least some mode(s) comprise the application of MEOA(s). In aspects, one or more physical components of the system also are changed (e.g., by the addition of a blower to supplement or replace a compressor, by the addition of components that accommodate a greater volume of enriched oxygen airflow delivery to a patient, or both). In aspects, such modified components are provided to a user along with an operating system upgrade to arrive at an enhanced POC having any of the above-described functions. In aspects, enrichment of a POC comprises modifying battery settings to provide for the better efficiency of POC batteries associated with use of MEOAs.

Typical POCs function by collecting ambient air from the environment, which consists of about 80% nitrogen and 20% oxygen, compressing the ambient air, removing some/most of the nitrogen from the airflow, and thereafter outputting an enriched oxygen airflow ("EOA"), and delivering the EOA to the patient through an interface, such as a nasal cannula. An EOA is an airflow that has a higher concentration of oxygen than is found in ambient air. For example, the system specifications for the Inogen One® G3 concentrator provides for an oxygen concentration of 87-93% at any of its 4 or 5 settings. Similarly, the Inogen One® G4 concentrator provides for an oxygen concentration of between 87-93% at any of its 3 settings. Further, the system specifications for the Inogen One® G5 concentrator provides for an oxygen concentration of between 87-93% at any of its 6 settings. An MEOA comprises a substantial reduction of oxygen concentration compared to, for example, the Inogen One® G5 concentrator, such as an oxygen concentration less than 48% or less than 47% (and typically greater than 30% or 31%, such as greater than 33%, such as greater than 37% or 38%, e.g., ~40-45%, ~40-47%, or about 40-48%).

An EOA can be classified as a highly enriched oxygen airflow ("HEOA") having an oxygen concentration of at least about 90% (such as in the Inogen One® series), an intensively enriched oxygen airflow ("IEOA") having an oxygen concentration of at least about 60% (but less than about 90%), or a moderately enriched oxygen airflow ("MEOA"), an airflow comprising an oxygen concentration typically of between about 33-48%, e.g., ~35-45%, e.g., about 37-43%, or about 39-41%.

Readers should note that sometimes the word "oxygen" is used in place of EOA, as is typical in the art. Skilled persons will understand when such a use of "oxygen" in this disclosure or the art actually is in reference to an EOA, not pure oxygen. However, oxygen concentrations, by contrast, such as described in the preceding paragraph, refer to the concentration of oxygen within an enriched oxygen airflow.

Known oxygen concentrators in the market, such as the Inogen One®, are typically HEOA systems (delivering oxygen in concentrations of about 90% or more). Methods/systems of the present invention, however, comprise the use of moderately enriched oxygen airflows (MEOA(s)) in one or more states of operation (modes). In aspects, methods/systems of the invention are configured to switch between delivery of an MEOA under certain conditions and an HEOA, IEOA, or both, under other conditions.

In aspects, the POC on average, most of the time, at least generally always, at least substantially always, or always operates a volume of less than about 50 decibels, such as less than about 40 decibels, such as less than about 38 decibels, such as about 35 decibels or less, e.g., about 30 decibels or less. In aspects, the POC generates significantly less noise, generates noise significantly less frequently, or both, when operating under normal operating conditions as compared to on market POCs, such as Inogen® POCs.

POCs typically comprise one or more battery units, which typically are rechargeable. In aspects, the battery life of a POC operating according to the invention will have a battery life that is ≥~20%, ≥~33%, or ≥50% longer than typical commercial POC batteries (e.g., having a typical 8-cell battery life or battery life in at least generally all or substantially all POCs of ≥5.5 hours, ≥~6 hours, ≥~6.5 hours, ≥~7 hours, per battery. In aspects, the POC will comprise multiple batteries or greater numbers of cells (e.g., 2, 3, or 4 batteries or ~12, 16, 24, or 32 cells, e.g., 6-36 cells or 8-24 cells, such as ~8-16 cells), and, accordingly, have an overall typical battery performance life (on average, generally in all devices, or substantially in all devices, for at least one of the treatment periods described here) of ≥~10 hours, ≥~12 hours, ≥~14 hours, ≥~18 hours, ≥~24 hours, ≥~30 hours, or ≥36 hours (without recharge). In aspects, the batteries of the portable oxygen concentrator require recharging on average less than every 15 hours. Typically, a battery can be recharged in about 2.5-5, 2-3.5, or 1.75-3/3.5 hours, and a collection of batteries can be recharged in 2.5-10, 3-8, 3.5-7.5, 3.5-7, 4-7, or 4-6 hours, using either AC or DC power. In aspects, POCs can be powered by AC power, DC power, or both, and in aspects can adapt to different power supplies (e.g., 100-240V, 50-60 Hz, based on sensor(s) that determine the type of direct power supply and adjust power parameters accordingly (e.g., for patients traveling between different countries). In aspects, the POC batteries can be charged while also operating (e.g., overnight). In aspects, the batteries comprise or consist of batteries contained in an external battery unit. In aspects, the external battery unit can be physically coupled to the POC. In aspects, the external battery unit can be linked to the POC by a flexible wire.

In aspects, the POC is equipped with equipment to facilitate transport. In aspects, the POC is small enough to fit within a backpack or even a small backpack, such as a "newsboy" backpack (sling-style pack).

In aspects, the POC of the present invention is characterized by the lack of one or more components, operating parameters, or a combination thereof, which are included in the prior art patent documents and other references cited and incorporated herein by reference.

The POC typically comprises a processor, memory, pre-programmed instructions, and one or more digital displays, alarm units, and either comprises sensors or is adapted to operate with connected sensors or associated sensors. The processor typically is rated for at least 2 years of continuous use, such as about 20,000 hours of continuous use (e.g., through product testing). The processor typically comprises Bluetooth compatibility with other devices or interfaces, e.g., a mobile device application, other sensor(s), or both, or a similar local communication protocol/method. In aspects, the device is connected to the internet via a secure internet of medical things protocol that protects patient confidentiality, as are known in the art. In aspects, such communication means allow the device to also send alarms or updates to other persons monitoring performance of the device and patient, such as family members, health care providers ("HCPs"), or both.

Modes and Mode Switching

In aspects, the system is configured to automatically change between continuous delivery and pulse delivery based on feedback from one or more sensors, e.g., a sensor associated with the oxygen delivery interface (e.g., a sensor regarding the timing, volume, or other aspects of breathing of the patient), such as when the patient's breathing meets or exceeds one or more parameters, such as when the patient's breathing meets or exceeds one or more pre-programmed breathing rate(s), volume(s), or similar threshold(s) (e.g., blood oxygen concentration).

"Continuous delivery" of oxygen means a substantially uninterrupted flow of oxygen to the patient, usually, mostly, generally, substantially, or only at a set volume of airflow (e.g., a rate measured in liters per minute). Continuous delivery mode(s) can be employed to deliver MEOA(s), IEOA(s), HEOA(s), or a combination thereof. In one aspect, continuous delivery at least sometimes, mostly, generally, substantially, or only comprises delivery of HEOA/IEOA, typically delivery of an IEOA. In aspects, most patients, generally all patients, or substantially all patients receive pulse delivery most of the time, generally all the time, or substantially all the time during treatment. True continuous flow modes are, accordingly, typically not intermittent. However, intermittent continuous flow methods also can be used in methods/systems of the invention, as discussed below.

In aspects, continuous delivery is applied, e.g., while the patient is sitting still or sleeping, e.g., as determined by one or more factors (breathing rate, movement, etc.), timers, or combinations thereof.

A POC can deliver any suitable volume of enriched oxygen airflow in continuous delivery. The volume will depend on the mode of operation of the POC, as continuous delivery can be performed using MEOA, or HEOA/IEOA, or both.

In one exemplary aspect, a POC is configured to deliver about 240-1200, such as about 240-1080, ~240-960, ~240-720, or ~240-640 mL of an EOA, per average respiration period (e.g., per every 3-6 seconds), such as 290-590 mL, such as 340-540 mL, or such as 390-490 mL of an EOA. In aspects, a POC is configured in continuous flow mode(s) to deliver ~250-1,000 mL of EOA, such as HEOA or IEOA to a patient per average respiration or deliver EOA at a rate of 5-10 LPM. In aspects, most of the time, generally all the time, substantially all the time, or all the time continuous flow mode(s) are employed the airflow delivered to the patient is HEOA or IEOA, and typically an IEOA (e.g., an IEOA at a volume of at least ~3 LPM or ~5 LPM, such as ≥~5 LPM, e.g., 2.5-10 LPM, 4-10 LPM, 5-10 LPM, 5-8.5 LPM, or 5-7.5 LPM). In aspects where MEOA is delivered continuously, flow rates can be at least about 7.5 LPM, such as at least about 8, 8.5, 9, or at least about 9.5 LPM (e.g., 8-10 LPM, 8-12 LPM, 7.5-12.5 LPM, or 9-12 LPM). In aspects, continuous flow mode(s) do not deliver MEOA. In aspects, continuous flow mode(s) comprise MEOA delivery.

In aspects, the patient occasionally has or is at risk of having an oxygen demand equivalent to delivery of 5 LPM IEOA or greater, and the method comprises triggers that cause a switch to continuous flow mode(s) at least a significant amount of time per treatment regimen, calendar quarter, or year (e.g., at least 5% of the time, or at least 10%, at least 15%, at least 20%, at least 25%, or at least 33% of days). In aspects, the patient has been diagnosed or self-diagnosed as being a "mouth breather," e.g., during sleep or other periods, and the method comprises application of continuous flow at least an appreciable or material amount of time during any such period. In aspects, the patient has sleep apnea or another disease/condition that requires use of a CPAP or BiPAP device and the method comprises application of continuous flow when such device(s) also are employed to treat the condition.

"Pulse delivery" of oxygen provides "puffs" or discrete "doses" of enriched oxygen with each patient inhalation, per a set time, or both. In aspects, a pulse delivery mode solely uses one or more forms of pulse delivery. In other aspects, pulse delivery modes use intermittent continuous flow methods. In still other aspects, pulse delivery modes use a hybrid of true pulse delivery and intermittent continuous flow delivery. In one aspect, a pulse delivery mode comprises a rest period between inhalations where no enriched oxygen airflow is released to the patient.

In one pulse delivery mode a fixed amount of oxygen is delivered each time an operationally linked sensor or set of sensors detects inhalation, and then stops until the person takes another breath (such modes are used in POCs comprising "oxygen conserver" systems). In aspects, pulse delivery mode(s) comprise demand delivery, where continuous EOA flow is delivered until the system detects that a user has exhaled (dual lumen technology uses such a delivery system). In aspects, pulse delivery mode(s) comprise hybrid delivery, where EOA is delivered as a pulse at the beginning and the system then employs a lower or declining continuous flow delivery until the user exhales (as is used in pneumatic conserver systems). In still another aspect, pulse delivery mode(s) comprise minute volume delivery, in which a fixed amount of EOA per minute is delivered, but with the volume depending on the breathing rate of the user (slower breathing rate being associated with larger amount of oxygen per breath; faster breathing rate associated with a smaller amount of oxygen per breath). In aspects, pulse delivery mode(s) comprise uniform pulse delivery, where the same volume of EOA is delivered with every breath, regardless of the breathing rate (slower breathing rate equals less oxygen delivery over the course of a minute; faster breathing rate equals more oxygen delivery over the course of a minute). Pulse delivery mode(s) typically do not comprise providing enriched oxygen airflow at a set level per minute like continuous delivery over sustained periods (e.g., longer than a patient breath, or more than 2, 3, or 4 patient breaths). In aspects, pulse delivery comprises more than one pulse delivery mode, each pulse delivery mode comprising different oxygen concentrations, different volumes of enriched oxygen airflow, or both. Pulse delivery accordingly promotes energy efficiency and a longer battery life. The ability to perform pulse oxygen delivery also distinguishes some POCs from other oxygen delivery systems that only operate in continuous delivery mode.

In aspects, methods of the invention or settings of systems comprise two or more pre-programmed pulse delivery settings. In aspects, one or more of the pre-programmed pulse delivery settings delivers the volume of EOA, concentration of oxygen in the EOA, or both, in response to one or more parameters, such as decreases in breathing rate (indicating, e.g., the subject is sleeping). In aspects, patients sleeping may receive such an "enhanced bolus" pulse delivery, continuous delivery, or both, e.g., during periods of lower/low normal oxygen/air intake, such as during sleep, or during periods in which breathing becomes shallow/difficult or less frequent. In aspects, such enriched airflow conditions are also applied when other low oxygen intake conditions are detected in a subject.

In aspects, the system or method is configured to deliver most, generally all, substantially all, or all the EOA within a set period, such as within about 500 milliseconds, about 400 milliseconds, or about 300 milliseconds of detection of inspiration, when in pulse delivery. In aspects, however, an appreciable amount, material amount, at least about 25%, at least about 33.33%, or most of the EOA delivered is delivered after about 400 milliseconds from detection of inspiration, such as in cases where assuring a higher volume of EOA is desired. The response time in detection of breathing is typically at least as good (e.g., at least as sensitive) as in the Inogen One® series POCs and typically uses the same or similar methods of detecting breathing rate.

A POC can deliver any suitable volume of oxygen in pulse mode(s). In aspects, the volume of EOA(s) delivered in a system/method is greater than that typically delivered in present commercial POCs, such as Inogen One® G Series POCs (e.g., a significant increase or an increase of at least about 10%, at least about 20%, at least about 25%, at least about 33%, at least about 40%, at least about 50%, at least about 66.66%, at least about 75%, at least about 90%, or at least about 100% (2x), such as at least about 50-125%, 65-115%, 70-110%, 80-110%, or 85-105% of the average or typical pulse delivery of Inogen One® POC systems.

A POC can deliver any suitable volume of EOA of any suitable oxygen concentration. Typically, an appreciable amount, a material amount, or more, such as at least about 25%, at least about 33.33%, or most of the EOA delivered in pulse delivery mode(s) of a method/system comprise MEOA. In aspects, a POC is configured to perform pulse delivery of about 80-240 mL of a MEOA to the patient per pulse in one or more mode(s), such as about 90-230 mL, such as about 100-220 mL, such as about 110-210 mL, such as about 120-200 mL, such as about 130-190 mL, such as about 140-180 mL, or such as 150-170 mL of a MEOA per pulse.

Efficient and Effective MEOA

In further aspects, methods/systems are configured to generate an MEOA comprising an oxygen concentration of between about 33-48%, such as between about 35-45%, or such as between about 37-42% and pulse delivering an effective amount, such as a therapeutically effective amount, of MEOA to the patient. An "effective amount" is an amount that is capable of significantly increasing oxygen in the patient. A "therapeutically effective amount" means an amount effective to treat or prevent the low oxygen condition, disease, or risk. In aspects, the amount of oxygen is an IEOA equivalent amount. Such an equivalent amount means an amount wherein the amount of oxygen delivered (e.g., in mmol oxygen) is about the same as, statistically not different from, clinically not different from (e.g., based on significant results in clinical or nonclinical tests) as application of IEOA under typical pulse conditions used in the market (e.g., about 1-5 LPM), or a combination thereof.

In aspects, an amount of enriched oxygen airflow delivered in the method or by the system comprises about 80-about 240 mL of the MEOA per inspiration, such as about 100-220 mL, such as about 120-200 mL, or such as about 140-180 mL per inspiration.

In aspects, MEOA(s) is/are delivered to the patient over a period of at least 1 month, such as at least one calendar quarter, at least 4 months, at least 6 months, or at least one year. In aspects, the methods/systems comprise testing the patient for tolerance of moderately enriched oxygen airflow under supervision of a healthcare provider before allowing the patient to self-manage the portable oxygen concentrator.

In aspects, when the MEOA is pulse administered, the present methods/systems can deliver a statistically similar amount of millimoles of oxygen per inspiration of MEOA as the average typically delivered average millimoles of oxygen in pulse administration of a typical volume of an HEOA or IEOA delivered to a patient using conventional POCs. In aspects, the amount of oxygen delivered to the patient per inspiration of MEOA is about the same as the amount of millimoles of oxygen delivered to the patient per inspiration from an HEOA concentrator having an oxygen concentration of at least about 90%.

In further aspects, the methods/systems are configured to administer between about 0.05 mmol to about 0.5 mmol of oxygen such as between about 0.08 to about 0.45, such as between about 0.1 to about 0.4, such as between ~0.15 to ~0.35 mmol, or such as between about 0.2 to about 0.3 mmol of oxygen to the patient. In yet another aspect, methods/systems are configured to administer approximately the same mmol of oxygen as administered by currently available HEOA systems such as an Inogen One® G POC.

Select System Components

Systems of the invention can comprise any suitable components found in POCs in the art. The features of select components are described briefly here.

Sensors

The methods/systems of the present invention utilize one or more sensor(s) configured to detect changes in or associated with a patient, the device, or both. In an aspect, sensor(s) detect one or more aspects of patient oxygen intake (e.g., oxygen concentration). In an aspect, the one or more sensors comprise breath/breathing rate sensors. Breath/breathing rate sensors monitor a user's breathing patterns and communicate with the system such that the user receives oxygen at a level correlated with the breath/breathing rate. In an aspect, the one or more breath/breathing rate sensors are configured to monitor breathing of the patient through the oxygen delivery interface and relay information to the controller such that the controller can determine whether one or more aspects of a user's breathing exceeds one or more pre-programmed thresholds. Such sensor(s) are known in the art and described/referenced in incorporated references.

In aspects, sensor(s) detect one or more features of the user's breathing that result in a change in airflow from an MEOA to an IEOA. In another aspect, the one or more breath/breathing rate sensors detect one or more features of the user's breathing that result in a change in airflow from an IEOA to an MEOA (examples of such sensors are described in U.S. Ser. No. 10/859,456). In yet another aspect, the one or more breath/breathing rate sensors detect one or more features of the user's breathing that result in a change in oxygen delivery from a pulse delivery to a continuous delivery or from a continuous delivery to a pulse delivery based on whether the breathing of the patient exceeds the one or more pre-programmed thresholds.

Nitrogen Adsorption Media

In general, the methods/systems of the invention can be practiced with any suitable method for enriching oxygen from air or simply while delivering an oxygen airflow comprising an oxygen concentration that is enriched with respect to atmospheric oxygen concentrations. One commonly employed method for obtaining EOAs is the use of NAMs.

In an aspect, the system comprises a nitrogen adsorption media system, such as a rapid swing nitrogen adsorption media system or any other suitable nitrogen adsorption system used in the art, such as the system used in Inogen® POCs. Any suitable type of nitrogen adsorption system can be used. Such systems and related principles/technology are described in, e.g., U.S. Pat. No. 7,763,103, GB955894, U.S. Pat. Nos. 4,971,609, 6,691,702, JP 2010-227517, U.S. Pat. No. 3,533,221, EP1401557, US 2012/0266883, U.S. Pat. No. 8,894,751, and WO2015015852. In aspects, the POC comprises a system that monitors the NAM and notifies the user when replacement or maintenance is required/beneficial.

NAMs are known in the art and generally any suitable NAM can be used in the systems/methods of the invention. Briefly, nitrogen adsorption media is configured to remove nitrogen from the ambient air when it is exposed to the ambient air and acted on by a pressurized air flow that is sent through the media. The pressurized airflow traps the nitrogen molecules found in the ambient air, while the remaining oxygen flows through, creating an enriched oxygen airflow. The nitrogen adsorption media can be comprised of one or more of any type of nitrogen adsorption media known in the art including zeolite minerals, such as zeolite 5A and zeolite13X, single-wall carbon nanotubes ("SWNTs"), and double-wall carbon nanotubes ("DWNTs").

Pressure Gradient Generating System

In an aspect, the system comprises a PGGS, which is a component of a NAM "system," and that is configured to provide a pressure gradient that is selectively isolated from the environment by at least one air enrichment area separator (e.g., through the use of a compressor). In an aspect, application of the pressure gradient to the nitrogen adsorption media causes release of an enriched oxygen airflow.

The air enrichment area separator can be any type of barrier or enclosure known in the art, such as one or more cylinders, tubes, or canisters, that are configured to isolate the pressure gradient from the outside environment.

The pressure needed in some systems of the invention is significantly less than in current on market systems, given the fact that lower oxygen concentrations can be used at least sometimes in operation (in a MEOA mode). In an aspect, the PGGS provides a pressure gradient in an amount of between about 10-30 PSI, such as 12-28 PSI, or such as 15-25 PSI to the nitrogen adsorption media. In aspects, the PGGS is set to sometimes, most of the time, generally always, or at least substantially always apply a pressure to a NAM that is at least about 15% less, at least about 25% less, at least about 33% less, or at least about 40% less than the pressure applied to an NAM in a conventional POC. In aspects, a POC may operate using a blower versus a compressor, at least some of the operating time, if not most of the time, generally all of the time, or at least substantially all of the time. In aspects, a compressor component of a POC is operated at a reduction in time, intensity, energy expenditure, speed, or any combination thereof in a system/method of the invention as compared to conventional POC systems (e.g., by a reduction of at least 10%, ≥15%, ≥20%, ≥25%, or ≥~33% in one, some, most, or all of such characteristics).

Patient Oxygen Delivery Interface

In a further aspect, the system comprises a PODI that is configured to administer the enriched oxygen to the patient. In an aspect, the breathing of the patient is monitored through the PODI to determine whether to switch between continuous delivery and pulse delivery of the oxygen and/or to determine the timing of one or more EOA dose administrations. The PODI can be any type of PODI known in the art such as a nasal cannula, a simple face mask, a partial rebreather face mask, a non-rebreather face mask, or a tracheostomy mask. In aspects, a system can be used with both a nasal cannula and mask PODI. In methods, most, generally all, or substantially all the time the patient receives EOA delivery through a nasal cannula. In an aspect the PODI is configured to fluidly connect to a flow line which is further configured to connect to an airflow outlet on the system. Such systems are known in the art.

Controller

In an aspect, the system comprises a programmable controller component, which further comprises stored computer-readable instructions (memory) and a processor component configured to read and execute the computer-readable instructions.

The controller typically is composed of machine-readable instructions encoded in physical, transferable, and reproducible or at least non-transient computer readable media and suitable computer processors. The controller of the POC can typically be considered a specialized computing device, in the sense that most, generally all, substantially all, or all of its encoding is configured for the control of the operation of the other components of the POC, such as the operation of the pressure gradient generating system, the delivery of the volume of oxygen to the patient, interfacing with sensor(s), relaying of display information in the POC or an associated specialized interface (such as a mobile phone application, web page, or both), triggering of POC alarm(s), and the like. The instruction component of the controller is typically programmable by a suitable programming language. Software/hardware systems are commonly used in modern POCs, such as Inogen® POCs, and examples of such systems have been described in the art (see, e.g., WO2020037375, WO2011127314, WO2019202390, U.S. Pat. Nos. 6,651,658, and 9,717,876).

In an aspect, the controller is configured to determine whether one or more aspects of the patient's breathing exceeds one or more thresholds. In an aspect, the controller is configured to control the volume of the airflow delivered to the patient and the oxygen concentration of the airflow delivered to the patient. In a further aspect, if the controller determines that the one or more aspects has exceeded the one or more thresholds, the controller is further configured to cause the system to automatically change between continuous and pulse delivery of oxygen through the PODI. In aspects, the invention comprises modifying the controller in such a manner so as to configure the POC to generate and deliver the EOA as described herein. Such modification(s) can, in aspects, be performed by the original POC manufacturer prior to sale of the POC. In aspects, such modification(s) can be made programmatically, e.g., through the modification of operational code, e.g., proprietary code, of the POC.

Illustrative Embodiments Shown in the Figures

FIG. 1 is an abstract representation of the application of principles underlying the methods and devices of the present invention. FIG. 1 shows two containers with varying volumes of air, representative of a unit volume of air delivered by a POC. The larger container on the left (100) is representative of the features of a unit volume of air provided by the present invention. The smaller container on the right (110) is representative of the features of a unit volume of air provided by a POC of the prior art (delivering at least 80% enriched oxygen). As shown by the dotted line (unlabeled) within the first container (100), the unit volume of air of the second, smaller container (110) is approximately half the size of the unit volume of air provided by the larger container. Diameter (140) further illustrates the equal diameters of each of the two representative unit volume containers. Containers (100) and (110) demonstrate the molar ratio of oxygen molecules within the two systems. The first container (100) illustrates the present invention providing oxygen in an amount of 4 molecules of enriched oxygen (120) per every 6 molecules of non-enriched or ambient air molecules (130), or a 40% moderately enriched oxygen concentration, while the second container (110) illustrates commercial systems as providing 8 molecules of enriched oxygen (130) per every 2 molecules of non-enriched or ambient air molecules (120), or a highly enriched 80% oxygen concentration. One can appreciate that a similar representation could be made illustrating a commercial system providing a more typical highly enriched (90%) oxygen concentration. The 80% enrichment was simply chosen for ease of presentation in this simple drawing. The unit volumes illustrated by FIG. 1 could be any unit volume. In other words, FIG. 1 is a simple figure used to aid in the understanding of the basic concepts underlying the lower concentration oxygen system(s) and device(s) provided by the invention.

Figure 2:
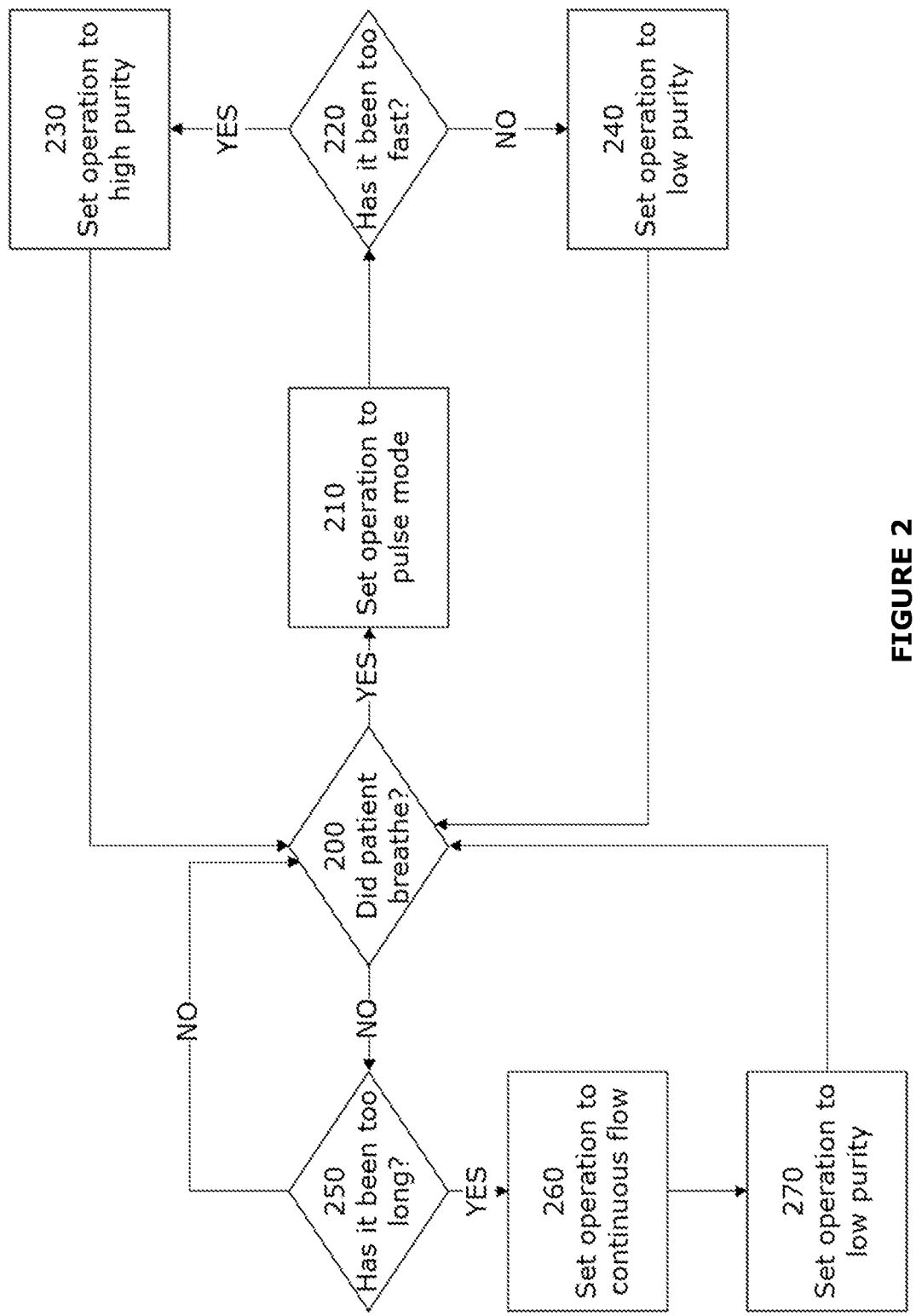
FIG. 2 is a flow chart representing the steps of operation of a portable oxygen concentrator according to aspects of the present invention.

FIG. 2 is a flow chart representing a process of using a portable oxygen concentrator according to aspects of the invention. Initially, an analysis is performed to determine whether a patient has taken a breath (200). If the patient has taken a breath, the operation of the portable oxygen concentrator is set to pulse mode (210). Once in pulse mode, an analysis is performed to assess whether the pulse is being administered too quickly (220). If the pulse is being administered too quickly, the operation is set to high purity (230). The process is then repeated to determine whether the patient has taken a breath (200). If so, the operation is again set to pulse mode (210). If upon analysis (220) it is determined that the pulse is not being administered too quickly, the operation is set to low purity (240). The process is then repeated to determine whether the patient has taken a breath (200). If upon analysis (200) it is determined that the patient has not taken a breath (no breathing is detected), an analysis is performed to determine whether the time between two breaths has passed a pre-established threshold (250). If the pre-established threshold has been surpassed, the operation of the portable oxygen concentrator is set to continuous flow (260). Once in continuous flow, operation is set to deliver high purity oxygen (270). The process is then repeated to determine whether the patient has taken a breath (200). If upon analysis it is determined that the pre-established threshold for time between two breaths has not been surpassed (250), the system again determines whether breathing is detected (200), and the full process described here is repeated.

Exemplary Aspects of the Invention

The following is a non-limiting list of aspects of the invention.

In one aspect the invention provides a method of assisting breathing in a chronic obstructive pulmonary disease patient having low blood oxygen saturation, the method comprising (a) providing the chronic obstructive pulmonary disease patient with a portable oxygen concentrator that delivers an enriched oxygen airflow, and which comprises: (1) a pressure gradient generating system, (2) at least one nitrogen adsorption media that generates an enriched oxygen airflow when exposed to air and acted on by a sufficient pressure gradient and that is selectively isolated from the environment by at least one air enrichment area separator, (3) an enriched oxygen airflow outlet that is fluidly connected to a flow line and a patient oxygen delivery interface (such as a nasal cannula), (4) a programmable controller comprising stored computer readable instructions and a processor for executing such instructions and that in operation determines (I) the volume of the airflow delivered to the patient, (II) the oxygen concentration of the airflow, and (III) whether to deliver enriched oxygen airflow to a patient either via continuous delivery or pulse delivery, and (5) one or more sensors configured to detect changes in patient oxygen intake, such as at least one breath/breathing rate sensor, (b) delivering an enriched oxygen airflow to the patient for a period of at least about 1 month, the delivery of the enriched oxygen airflow comprising (I) generating a moderately enriched oxygen airflow comprising an oxygen concentration of 33-48%, and (II) pulse delivering to the patient about 80-about 240 mL of the moderately enriched airflow per inspiration, wherein the average millimoles of oxygen delivered to the patient per inspiration is statistically similar to the amount of millimoles of oxygen delivered to the patient per inspiration of a highly enriched oxygen airflow having an oxygen concentration of about 90%, (c) monitoring breathing of the patient through the patient oxygen delivery interface, and (d) automatically changing between continuous delivery and pulse delivery based on the timing of the detection of breathing of the patient through the patient oxygen delivery interface when the controller determines that one or more aspects of the patient's breathing exceeds one or more pre-programmed thresholds (aspect 1).

In one aspect, the invention provides the method of aspect 1, wherein in continuous delivery the portable oxygen concentrator delivers about 240-640 mL of either an intensively enriched oxygen airflow or highly enriched oxygen airflow (aspect 2).

In one aspect, the invention provides the method of aspect 1 or aspect 2, wherein the portable oxygen concentrator switches from pulse delivery to continuous delivery or vice versa at least once per day (e.g., 24-hour interval) on average during the at least 1-month period (aspect 3).

In one aspect, the invention provides the method of any one of aspects 1-3, wherein the method further comprises automatically changing the oxygen content of the portable oxygen concentrator's airflow from a moderately enriched oxygen airflow to an intensively enriched oxygen airflow or highly enriched oxygen airflow based on the detection of one of more conditions (aspect 4).

In one aspect, the invention provides the method of any one of aspects 1-4, wherein the method further comprises automatically changing the airflow from an intensively enriched oxygen airflow or highly enriched oxygen airflow to a moderately enriched oxygen airflow based on the detection of one or more conditions comprising one or more breath/breathing rate conditions in the patient (aspect 5).

In one aspect, the invention provides the method of any one of aspects 1-5, wherein the average rate of enriched airflow to the patient in continuous delivery, pulse delivery, or both, is at least about 3.3 L/minute (aspect 6).

In one aspect, the invention provides the method of aspect 6, wherein the average rate of enriched airflow to the patient in continuous delivery, pulse delivery, or both, is greater than 3.6 L/minute (aspect 7).

In one aspect, the invention provides the method of any one of aspects 1-7, wherein the average oxygen intake per inspiration of the patient is about 0.05 mmol to about 0.5 mmol oxygen (aspect 8).

In one aspect, the invention provides the method of any one of aspects 1-8, wherein the method comprises operating the pressure gradient system at least about 33% longer, opening the air enrichment area separator at least about 33% longer, or both, as compared to the default operating parameters of an Inogen G3, Inogen G4, or Inogen G5 POC (aspect 9).

In one aspect, the invention provides the method of any one of aspects 1-9, wherein the method comprises applying a pressure gradient comprising a maximum pressure of between 10-30 PSI to the nitrogen adsorption media (aspect 10).

In one aspect, the invention provides the method of aspect 10, wherein the delivery of oxygen consumes an average of between about 30-90, Watts of energy, such as between about 30-60 Watts of energy (aspect 11).

In one aspect, the invention provides the method of any one of aspects 1-11, wherein the concentration of oxygen in the moderately enriched airflow is about 40% and the average volume of moderately enriched airflow delivered per inspiration is between about 40 mL to about 520 mL (aspect 12).

In one aspect, the invention provides the method of any one of aspects 1-12, wherein the average volume of moderately enriched airflow delivered per inspiration is between about 150-350 mL (aspect 13).

In one aspect, the invention provides the method of aspect 13, wherein the average volume of moderately enriched airflow delivered per inspiration thereof is at least about 200 mL (aspect 14).

In one aspect, the invention provides the method of aspect 14, wherein the average volume of moderately enriched airflow delivered per inspiration is at least about 300 mL (aspect 15).

In one aspect, the invention provides the method of any one of aspects 1-15, wherein the patient has an average blood oxygen saturation of lower than about 93% or 92%, such as about 88%-92%, at the start of the method (aspect 16).

In one aspect, the invention provides the method of any one of aspects 1-16, wherein the method comprises testing the patient for tolerance of moderately enriched oxygen airflow under supervision of a healthcare provider before allowing the patient to self-manage the portable oxygen concentrator (aspect 17).

In one aspect, the invention provides the method of any one of aspects 1-17, wherein the portable oxygen concentrator generates an average of less than 50 decibels of noise in operation (aspect 18).

In one aspect, the invention provides the method of any one of aspects 1-18, wherein the method is performed for a period of at least about 6 months (aspect 19).

In one aspect, the invention provides the method of any one of aspects 1-19, wherein the airflow to the patient consists essentially of oxygen enriched air (aspect 20).

In one aspect, the invention provides a system for increasing oxygen intake in a patient requiring oxygen supplementation comprising a portable oxygen concentrator device configured to provide the patient with an enriched oxygen airflow, the portable oxygen concentrator comprising (a) a pressure gradient generating system, (b) at least one nitrogen adsorption media configured to generate an enriched oxygen airflow when exposed to air and acted on by a sufficient pressure gradient and that is selectively isolated from the environment by at least one air enrichment area separator, (c) an enriched oxygen airflow outlet that is fluidly connected to a flow line and a patient oxygen delivery interface, (d) a programmable controller comprising stored computer readable instructions and a processor to determine (1) the volume of the airflow delivered to the patient, (2) the oxygen concentration of the airflow, and (3) to cause delivery of enriched oxygen airflow to a patient either via continuous or pulse delivery, and (e) one or more sensors configured to detect changes in patient oxygen intake, such as at least one breath/breathing rate sensor, wherein in operation (1) the controller controls the operation and operating conditions of the pressure gradient generating system, the at least one air enrichment area separator, the enriched oxygen airflow outlet, and the oxygen delivery interface, (2) the one or more sensors are configured to monitor breathing of the patient through the oxygen delivery interface and determine whether one or more aspects of a user's breathing exceeds one or more pre-programmed thresholds, (3) the controller causes the delivery of enriched oxygen to change from a pulse delivery to a continuous delivery and back again based on whether the breathing of the patient exceeds the one or more pre-programmed thresholds, and (4) in pulse delivery the system generates and delivers a moderately enriched oxygen airflow comprising between 33-48% oxygen and delivers the moderately enriched oxygen airflow in pulses of about 80-about 240 mL (aspect 21).

In one aspect, the invention provides the system of aspect 21, wherein the portable oxygen concentrator is configured to deliver to the patient about 240-640 mL of an intensively enriched oxygen airflow or highly enriched oxygen airflow (aspect 22).

In one aspect, the invention provides the system of aspect 21 or aspect 22 wherein the portable oxygen concentrator is configured to switch from pulse delivery to continuous delivery, from continuous delivery to pulse delivery, or any combination thereof, at least once per 24-hour interval on average (aspect 23).

In one aspect, the invention provides the system of any one of aspects 21-23 wherein the portable oxygen concentrator is configured to change the airflow from the moderately enriched oxygen airflow to the intensively enriched airflow or highly enriched oxygen airflow, from the intensively enriched oxygen airflow or highly enriched oxygen airflow to the moderately enriched oxygen airflow, or any combination thereof, based on the detection of one of more system or patient conditions (aspect 24).

In one aspect, the invention provides the system of any one of aspects 21-24, wherein the average rate of enriched airflow to the patient in continuous delivery, pulse delivery, or both, is at least about 3.3 L/minute (aspect 25).

In one aspect, the invention provides the system of aspect 25, wherein the average rate of enriched airflow to the patient in continuous delivery, pulse delivery, or both, is greater than 3.6 L/minute (aspect 26).

In one aspect, the invention provides the system of any one of aspects 21-26, wherein the system is configured to deliver an average volume of about 0.05 mmol to about 0.5 mmol of moderately enriched airflow, per inspiration of the patient (aspect 27).

In one aspect, the invention provides the system of any one of aspects 21-27, wherein the pressure gradient applied to the nitrogen adsorption media comprises a maximum pressure of between 15-25 PSI (aspect 28).

In one aspect, the invention provides the system of any one of aspects 21-28, wherein the delivery of oxygen consumes an average of about 30-90, such as 30-60 Watts of energy (aspect 29).

In one aspect, the invention provides the system of any one of aspects 21-29, wherein the system is configured to provide a moderately enriched airflow oxygen concentration of about 40% and to deliver an average volume of about 40 mL to about 520 mL of moderately oxygen enriched airflow per inspiration of the patient (aspect 30).

In one aspect, the invention provides the system of any one of aspects 21-30 wherein the system is configured to deliver an average volume of between about 150-350 mL of moderately oxygen enriched airflow per inspiration of the patient when delivering a moderately oxygen enriched airflow (aspect 31).

In one aspect, the invention provides the system of aspect 31, wherein the system is configured to deliver an average volume of at least about 200 mL of moderately oxygen enriched airflow per inspiration of the patient when delivering a moderately oxygen enriched airflow (aspect 32).

In one aspect, the invention provides the system of aspect 32, wherein the system is configured to deliver an average volume of at least about 300 mL of moderately enriched airflow per inspiration of the patient when delivering a moderately oxygen enriched airflow (aspect 33).

In one aspect, the invention provides the e system of any one of aspects 21-33, wherein the operating conditions for the system comprise operating the pressure gradient system at least about 33% longer, opening the air enrichment area separator at least about 33% longer, or both, as compared to the default operating parameters of an Inogen One® G3, Inogen One® G4, or Inogen One® G5 POC (aspect 34).

What is claimed is:

1. A method of assisting breathing in a patient having low blood oxygen saturation, the method comprising:
    (a) providing the patient with a portable oxygen concentrator that delivers an enriched oxygen airflow, wherein the portable oxygen concentrator comprises:
        (1) a pressure gradient generating system,
        (2) at least one nitrogen adsorption media that generates the enriched oxygen airflow when exposed to air and acted on by a sufficient pressure gradient and that is selectively isolated from an ambient environment by at least one air enrichment area separator,
        (3) an enriched oxygen airflow outlet that is fluidly connected to a flow line and a patient oxygen delivery interface, and
        (4) a programmable controller comprising stored computer readable instructions and a processor for executing such instructions and that in operation determines
            (I) a volume of the airflow delivered to the patient,
            (II) an oxygen concentration of the airflow, and
            (III) whether to deliver enriched oxygen airflow to the patient either via continuous delivery or a pulse delivery, and
        (5) one or more sensors configured to detect changes in patient oxygen intake,
    (b) delivering an enriched oxygen airflow to the patient for a period of at least 1 month, the delivery of the enriched oxygen airflow comprising
        (1) generating a moderately enriched oxygen airflow comprising an oxygen concentration of 33-48%, and
        (2) pulse delivering to the patient at least about 300 mL of the moderately enriched oxygen airflow per average inspiration of the patient in at least one pulse delivery mode,
    (c) automatically monitoring breathing of the patient through the one or more sensors configured to detect changes in patient oxygen intake,
    (d) automatically changing between the at least one pulse delivery mode and a continuous delivery mode wherein the continuous delivery mode comprises the portable oxygen concentrator automatically
        (1) generating an intensively enriched oxygen airflow comprising an oxygen concentration of at least about 60% and
        (2) continuously delivering between about 640 ml and about 1200 ml of the intensively enriched oxygen airflow per average inspiration to the patient based on a timing of the detection of breathing of the patient through the one or more sensors when the controller determines that one or more aspects of the patient's breathing meets or exceeds one or more pre-programmed thresholds, and (e) operating the portable oxygen concentrator at up to 3.125 watts per liter per minute.

2. The method of claim 1, wherein the patient is a chronic obstructive pulmonary disease patient.

3. The method of claim 1, wherein the oxygen concentration of the intensively enriched oxygen airflow is at least about 75%.

4. The method of claim 1, wherein the continuous delivery mode comprises delivering the intensively enriched oxygen airflow to the patient at a rate of at least 10.45 LPM.

5. The method of claim 3, wherein the continuous delivery mode comprises delivering the intensively enriched oxygen airflow to the patient at a rate of at least 10.45 LPM.

6. The method of claim 1, wherein the continuous delivery mode comprises delivering a highly enriched oxygen airflow comprising an oxygen concentration of at least about 90% to the patient.

7. The method of claim 1, wherein the portable oxygen concentrator detects patient inspirations and automatically delivers at least about 75% of a pulse of moderately enriched oxygen within about 500 milliseconds of detection of an inspiration.

8. The method of claim 7, wherein the portable oxygen concentrator detects patient inspirations and automatically delivers at least about 75% of the pulse of moderately enriched oxygen within about 300 milliseconds of detection of an inspiration.

9. The method of claim 1, wherein generating the moderately enriched oxygen airflow comprises applying the pressure gradient at a maximum pressure of between 15-25 PSI to the nitrogen adsorption media.

10. The method of claim 1, wherein the portable oxygen concentrator is configured to switch from the at least one pulse delivery mode to the continuous delivery mode or vice versa at least once per 24-hour interval on average during the at least 1-month period.

11. The method of claim 1, wherein the one or more sensors detect patient inhalation and exhalation and the at least one pulse delivery mode comprises delivering an initial pulse of oxygen upon detection of inhalation and thereafter delivering a declining continuous flow of an enriched oxygen airflow until the sensor detects that the patient has exhaled.

12. A method of assisting breathing in a patient having low blood oxygen saturation, the method comprising:
(a) providing the patient with a portable oxygen concentrator that delivers an enriched oxygen airflow, wherein the portable oxygen concentrator comprises:
(1) a pressure gradient generating system,
(2) at least one nitrogen adsorption media that generates an enriched oxygen airflow when exposed to air and acted on by a sufficient pressure gradient and that is selectively isolated from the ambient environment by at least one air enrichment area separator, and
(3) an enriched oxygen airflow outlet that is fluidly connected to a flow line and a patient oxygen delivery interface,
(b) causing the portable oxygen concentrator to deliver an enriched oxygen airflow to the patient for a period of at least 1 month, the delivery of the enriched oxygen airflow comprising
(1) generating a moderately enriched oxygen airflow comprising an oxygen concentration of 33-48% and
(2) pulse delivering to the patient at least about 300 ml of the moderately enriched oxygen airflow per average inspiration of the patient, and
(3) changing between pulse delivering the moderately enriched oxygen airflow and a continuous delivery mode wherein the continuous delivery mode comprises the portable oxygen concentrator automatically
(I) generating an intensively enriched oxygen airflow comprising an oxygen concentration of at least about 60% and
(II) continuously delivering between about 640 ml and about 1200 ml of the intensively enriched oxygen airflow per average inspiration to the patient, and
(c) operating the portable oxygen concentrator at up to 3.125 watts per liter per minute.

13. The method of claim 12, wherein the patient is a chronic obstructive pulmonary disease patient.

14. The method of claim 12, wherein the portable oxygen concentrator detects patient inspirations and automatically delivers at least about 75% of a pulse of moderately enriched oxygen within about 500 milliseconds of detection of an inspiration.

15. The method of claim 14, wherein the portable oxygen concentrator detects patient inspirations and automatically delivers at least about 75% of the pulse of moderately enriched oxygen within about 300 milliseconds of detection of an inspiration.

* * * * *